(12) United States Patent
During

(10) Patent No.: US 10,188,635 B2
(45) Date of Patent: *Jan. 29, 2019

(54) USE OF GABOXADOL IN THE TREATMENT OF TINNITUS

(71) Applicant: Ovid Therapeutics Inc., New York, NY (US)

(72) Inventor: Matthew During, Weston, CT (US)

(73) Assignee: OVID THERAPEUTICS INC., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/056,754

(22) Filed: Aug. 7, 2018

(65) Prior Publication Data

US 2018/0344709 A1 Dec. 6, 2018

Related U.S. Application Data

(63) Continuation of application No. 15/873,425, filed on Jan. 17, 2018, now Pat. No. 10,071,083.

(60) Provisional application No. 62/454,280, filed on Feb. 3, 2017, provisional application No. 62/530,528, filed on Jul. 10, 2017, provisional application No. 62/536,669, filed on Jul. 25, 2017.

(51) Int. Cl.
   *A61K 31/437* (2006.01)
   *A61K 31/5513* (2006.01)
   *A61P 27/16* (2006.01)

(52) U.S. Cl.
   CPC ........ *A61K 31/437* (2013.01); *A61K 31/5513* (2013.01); *A61P 27/16* (2018.01); *A61K 2300/00* (2013.01)

(58) Field of Classification Search
   CPC .................................................. A61K 31/437
   See application file for complete search history.

(56) References Cited

U.S. PATENT DOCUMENTS

| | | |
|---|---|---|
| 2,830,083 A | 4/1958 | Gilbert et al. |
| 3,947,579 A | 3/1976 | Fuxe |
| 4,278,676 A | 7/1981 | Krogsgaard-LarsenPovl |
| 4,353,910 A | 10/1982 | Perregaard |
| 4,362,731 A | 12/1982 | Hill |
| 6,461,644 B1 | 10/2002 | Jackson et al. |
| 9,339,495 B2 | 5/2016 | During |
| 9,351,968 B1 | 5/2016 | During |
| 9,399,034 B1 | 7/2016 | During et al. |
| 9,446,028 B2 | 9/2016 | During |

(Continued)

FOREIGN PATENT DOCUMENTS

| | | |
|---|---|---|
| EP | 0000338 A3 | 6/1979 |
| EP | 0840601 B1 | 10/2001 |

(Continued)

OTHER PUBLICATIONS

Zarenoe et al., Auris Nasus Larynx, 2013;40:41-45 (Year: 2013).

(Continued)

*Primary Examiner* — San Ming R Hui

(74) *Attorney, Agent, or Firm* — Carter, DeLuca, Farrell & Schmidt, LLP

(57) ABSTRACT

Methods of treating tinnitus with gaboxadol or a pharmaceutically acceptable salt thereof are provided. The methods provide therapeutic compositions that may be used to improve one or more symptoms of tinnitus.

15 Claims, 2 Drawing Sheets

(56) References Cited

U.S. PATENT DOCUMENTS

| | | | |
|---|---|---|---|
| 9,682,069 | B2 | 6/2017 | During |
| 9,717,716 | B2 | 8/2017 | During et al. |
| 10,071,083 | B2 | 9/2018 | During |
| 2003/0077297 | A1 | 4/2003 | Chen et al. |
| 2007/0032553 | A1* | 2/2007 | McKernan ........... A61K 31/437 514/561 |
| 2007/0112017 | A1 | 5/2007 | Barlow et al. |
| 2007/0259912 | A1 | 11/2007 | Cooper |
| 2008/0255096 | A1 | 10/2008 | Knipper-Breer |
| 2008/0269278 | A1 | 10/2008 | Lundahl et al. |
| 2009/0143335 | A1 | 6/2009 | Larsen et al. |
| 2010/0029770 | A1 | 2/2010 | Roberts et al. |
| 2010/0297181 | A1 | 11/2010 | Hanada et al. |
| 2011/0046090 | A1 | 2/2011 | Barlow et al. |
| 2012/0035207 | A1 | 2/2012 | McKernan et al. |
| 2012/0302554 | A1 | 11/2012 | Knipper-Breer et al. |
| 2013/0251671 | A1 | 9/2013 | Kaufman et al. |
| 2014/0371210 | A1 | 12/2014 | Battaglia |
| 2015/0352085 | A1 | 12/2015 | During |
| 2016/0038469 | A1 | 2/2016 | During |
| 2016/0228418 | A1 | 8/2016 | During |
| 2017/0014392 | A1 | 1/2017 | During |
| 2017/0014393 | A1 | 1/2017 | During |
| 2017/0042863 | A1 | 2/2017 | During et al. |
| 2017/0348232 | A1 | 12/2017 | During |
| 2018/0042903 | A1 | 2/2018 | During |
| 2018/0235942 | A1 | 8/2018 | During et al. |

FOREIGN PATENT DOCUMENTS

| | | | |
|---|---|---|---|
| GB | 2410434 | A | 8/2005 |
| WO | 9702813 | A1 | 1/1997 |
| WO | 2005023256 | A1 | 3/2005 |
| WO | 2005094820 | A1 | 10/2005 |
| WO | 2006079476 | A1 | 8/2006 |
| WO | 2009080268 | A1 | 7/2009 |
| WO | 2013056159 | A1 | 4/2013 |
| WO | 2015189744 | A1 | 12/2015 |

OTHER PUBLICATIONS

Complete guide to different types of hearing loss, https://www.earq.com/blog/complete-guide-to-hearing-loss-types, 2015 (Year: 2015).

Cheng et al., "Inducing Anesthesia with a GABA Analog, THIP,", Anesthesiology, vol. 63, No. 2, Aug. 1985; pp. 147-151.

Ebert et al., "Treating Insomnia: Current and Investigational Pharmacological Approaches," Pharmacology & Therapeutics, vol. 112, 2006; pp. 612-629.

McCaffery et al.,, "Policy and Procedure on Conscious Sedation/Analgesia for Adults," Pain: Clinical Manual (1996); 10 pages.

Sessler et al., Semin. Respir. Crit. Care Med. (2013), vol. 34(2), pp. 169-178.

Walsh et al., "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.

Stephanie Saul, "Merck Cancels Work on a New Insomnia Medication," The New York Times, Business Day, Mar. 29, 2007; http://www.nytimes.com/2007/03/29/business/29sleep.html?.sub.-r=0; 3 pages.

Ransdell Pierson, Update 2-Merck, Lundbeck scrap insomnia drug after trials, Rueters, (Dow Jones); 2015; 2 pages.

Egawa et al., Decreased Tonic Inhibition in Cerebellar Granule Cells Causes Motor Dysfunction in a Mouse Model of Angelman Syndrome, Neurodegenerative Disease, Science Translational Medicine, vol. 4, Issue 165 (163ra157), Dec. 5, 2012. pp. 1-10.

James K. Walsh, Ph.D., "Enhancement of Slow Wave Sleep: Implications for Insomnia," Journal of Clinical Sleep Medicine, Supplement to vol. 5, No. 2, (2009); pp. 827-832.

International Search Report and Written Opinion of the International Searching Authority, dated Aug. 26, 2015, corresponding to International Application No. PCT/US15/34018; 12 total pages.

Olmos-Serrano et al, "Defective GABAergic Neurotransmission and Pharmacological Rescue of Neuronal Hyperexcitability in the Amygdala in a Mouse Model of Fragile X Syndrome," The Journal of Neuroscience, vol. 30, No. 29, Jul. 21, 2010; pp. 9929-9938(25 pages).

Walter Alexander, "Sleep: Gaboxadol Enhances Slow Wave Sleep," Perelman, School of Medicine, Jun. 22, 2006; 3 pages.

Brown et al., "Pharmacological Characterization of a Novel Cell Line Expressing Humanα4β3δ GABAA Receptors," British Journal of Pharmacology, vol. 136, No. 7, 2002; pp. 965-974.

Deacon et al., "Effect of Short-Term Treatment with Gaboxadol on Sleep Maintenance and Initiation in Patients with Primary Insomnia," Sleep, vol. 30, No. 3, 2007; pp. 281-287.

Faulhaber et al., "The GABAA Agonist THIP Produces Slow Wave Sleep and Reduces Spindling Activity in NREM Sleep in Humans," Psychopharmacology, vol. 130, 1997; pp. 285-291.

Gaboxadol, from Wikipedia, the free encyclopedia, http://en.wikipedia.org/wiki/Gaboxadol, 2014; 2 pages.

Gaboxadol, Investigational Agent—Drug Development Technology, http//www.drugdevelopment-technology.com/projects/gaboxadol—2014; 3 pages.

Gaboxadol, Bluelight, http://www.bluelight.org/vb/threads/370965-Gaboxadol—(2014); 1 page.

Glykys et al., "The Main Source of Ambident GABA Responsible for Tonic Inhibition in the Mouse Hippocampus," J Physiol, vol. 582, No. 3, 2007; pp. 1163-1178.

Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.

Iber et al., "The AASM Manual for the Scoring of Sleep and Associated Events," American Academy of Sleep Medicine (2007); pp. 3-59 (57 pages).

Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.

Jonas et al., "Neural Inhibition,", Scholarpedia—http://www.scholarpedia.org/article/Neural.sub.-inhibition- —(2014); 10 pages.

Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.

Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.

Marike Lancel, "Role of GABAA Receptors in the Regulation of Sleep: Initial Sleep Responses to Peripherally Administered Modulators and Agonists," Sleep, vol. 22, No. 1, (1999); pp. 33-42.

Lancel et al., "Effect of the GABAA Agonist Gaboxadol on Nocturnal Sleep and Hormone Secretion in Healthy Elderly Subjects," Am J. Physiol Endoctrinol Metab, vol. 281; (2001), pp. E130-E137.

Larsen et al.,—Research Paper—"Intestinal Gaboxadol Absorption via PAT1 (SLC36A1): Modified Absorption in vivo Following Co-administration of L-tryptophan," British Journal of Pharmacology (BJP), vol. 157, (2009); pp. 1380-1389.

Lundahl et al., "Short-term Treatment with Gaboxadol Improves Sleep Maintenance and Enhances Slow Wave Sleep in Adult Patients with Primary Insomnia," Psychopharmacology, vol. 195, (2007); pp. 139-146.

Mathias et al., "The GABAA Agonist Gaboxadol Improves the Quality of Post-Nap Sleep," Psychopharmacology, vol. 157 (2001); pp. 299-304.

Mathias et al., "Effect of Repeated Gaboxadol Administration on Night Sleep and Next-Day Performance in Healthy Elderly Subjects," Neuropsychopharmacology, vol. 30, (2005) pp. 833-841.

Olmos-Serrano et al, "The GABAA Receptor Agonist THIP Ameliorates Specific Behavioral Deficits in the Mouse Model of Fragile X Syndrome," Developmental Neuroscience, vol. 33, Fragile X Syndrome/Review, (2011), pp. 395-403.

(56) References Cited

OTHER PUBLICATIONS

Tropea et al., "Partial Reversal of Rett Syndrome-like Symptoms in MeCP2 Mutant Mice," PNAS, vol. 106, No. 6, Feb. 10, 2009; pp. 2029-2034.
Boyle et al., "Next-day residual effects of gaboxadol and flurazepam administered at bedtime: a randomized double-blind study in healthy elderly subjects," Human Psychopharmacology, 2009, vol. 24, pp. 61-71.
Chaturvedi et al., "Fast Dissolving Films: A Review," Current Drug Delivery, 2011, vol. 8; pp. 373-380.
Ciper and Bodmeier, "Preparation and characterization of novel fast disintegrating capsules (Fastcaps) for administration in the oral cavity," Science Direct, International Journal of Pharmaceutics, 2005, vol. 303; pp. 62-71.
Boateng et al., "Characterisation of freeze-dried wafers and solvent evaporated films as potential drug delivery systems to mucosal surfaces," International Journal of Pharmaceutics, vol. 389, Issues 1-2, Apr. 15, 2010, pp. 24-31.
Journal of Labelled Compounds and Radiopharmaceuticals, 1982, vol. 19, No. 5; pp. 689-702.
Sametsky et al., "Enhanced GABAA-Mediated Tonic Inhibition in Auditory Thalamus of Rats with Behavioral Evidence of Tinnitus", The Journal of Neuroscience, vol. 35, No. 25, Jun. 24, 2015; pp. 9369-9380.
Richardson et al., "Targeting Inhibitory Neurotransmission in Tinnitus", Elsevier, SciVerse ScienceDirect, Brain Research 1485, Feb. 2012; pp. 77-87.
International Search Report and Written Opinion, dated Oct. 31, 2017, corresponding to International Application No. PCT/US17/46256; 10 total pages.
Yang et al, "Homeostatic plasticity drives tinnitus perception in an animal model", PNAS, Sep. 5, 2011, vol. 108, No. 36, pp. 14974-14979.
Richardson et al., "Extrasynaptic GABAA Receptors and Tonic Inhibition in Rat Auditory Thalamus", PLOS One, Jan. 2011, vol. 6, Issue 1, (e16508); pp. 1-5.
International Search Report and Written Opinion of the International Searching Authority, dated Apr. 24, 2018, corresponding to International Application No. PCT/US18/16602; 15 total pages.
Vardya et al., "Positive Modulation of δ-Subunit Containing GABAA Receptors in Mouse neurons" Neuropharmacology, vol. 63; 2012; pp. 469-479.
International Search Report and Written Opinion of the International Searching Authority, dated Sep. 27, 2016, corresponding to International Application No. PCT/US16/42238; 8 total pages.
Egawa et al., "Pathophysiological power of improper tonic GABA(A) conductances in mature and immature models." Frontiers in Neural Circuits, Oct. 2013, vol. 7, Article 170; pp. 1-15.
PCT Notice concerning Transmittal of International Preliminary Report on Patentability (Chapter I of the Patent Cooperation Treaty), International Preliminary Report on Patentability and Written Opinion of the International Searching Authority, dated Feb. 1, 2018, corresponding to International Application No. PCT/US2016/042238; 8 total pages.
Reagan-Shaw et al., "Dose translation from animal to human studies revisited", FASEB J, vol. 22, No. 3, Oct. 17, 2007; pp. 659-661.
International Search Report and Written Opinion of the International Searching Authority, dated Aug. 14, 2015, corresponding to International Application No. PCT/US2015/029155; 19 total pages.
Chian-Fourney et al., "Differential Regulation of Hippocampal BDNF mRNA by Typical and Atypical Antipsychotic Administration," Brain Research, vol. 954, No. 1, Nov. 1, 2002, Elsevier, pp. 11-20.
Boast et al., "5HT Antagonists Attenuate MK801-Impaired Radial Arm Maze Performance in Rats," Neurobiology of Learning and Memory, vol. 71, No. 3, May 1, 1999; pp. 259-271.
C. Idzikowski et al., "5-Hydroxytryptamine-2 Antagonist Increases Human Slow Wave Sleep," Brain Research, vol. 378, No. 1, Jul. 16, 1986, Elsevier, pp. 164-168.
Nagar et al., "Orally disintegrating tablets: formulation, preparation techniques and evaluation", Journal of Applied Pharmaceutical Science, vol. 01, No. 04, 2011; pp. 35-45.
Gupta Nitan Bharti et al., "Pulsatile Drug Delivery as Modified Release Dosage Form: A Review", Journal of Drug Delivery & Therapeutics, vol. 2, No. 6, 2012; pp. 102-110.
Reddy et al., "Review On: Pulsatile Drug Delivery Systems", Journal of Pharmaceutical Sciences and Research, (ISSN: 0975-1459), vol. 1, No. 4, 2009; pp. 109-115.
The United States Pharmacopeia (USP) disintegration test method set forth at section 701 Disintegration, Revision Bulletin Official Aug. 1, 2008; pp. 1-3.
Bharawaj et al., "Orally Disintegrating Tablets: A Review", Drug Invention Today, vol. 2, No. 1, (ISSN: 0975-7619), 2010; pp. 81-88.
Boyle et al., "Tolerability, pharmacokinetics and night-time effects on postural sway and critical flicker fusion of gaboxadol and zolpidem in elderly subjects," British Journal of Clinical Pharmacology, 2008, vol. 67, No. 2; pp. 180-190.
Guidance for Industry, Orally Disintegrating Tablets, United States Department of Health and Human Services, Food and Drug Administration, Center for Drug Evaluation and Research (CDER), Dec. 2008, Chemistry, pp. 1-8.
Yapar et al., "Orally Disintegrating Tablets: An Overview," Journal of Applied Pharmaceutical Science, Feb. 2014, vol. 4, No. 02, pp. 118-125.
Fu et al., "Drug Release Kinetics and Transport Mechanisms of Non-degradable and Degradable Polymeric Delivery Systems," NIH Public Access, Author Manuscript, National Institute of Health, Expert Opin Drug Deliv., Apr. 2010; vol. 7, No. 4 (pp. 429-444) 28 pages.
Kesisoglou et al., "Utility of PBPK Absorption Modeling to Guide Modified Release Formulation Development of Gaboxadol, a Highly Soluble Compound with Region-Dependent Absorption," Research Article—Pharmaceutics, Drug Delivery and PharmaceuticalTechnology, Aug. 19, 2015; Journal of Pharmaceutical Sciences, vol. 105 (2016); pp. 722-728 (7 pages).

* cited by examiner

2/2

USE OF GABOXADOL IN THE TREATMENT OF TINNITUS

CROSS REFERENCE TO RELATED APPLICATIONS

This application is a continuation application of U.S. patent application Ser. No. 15/873,425, filed Jan. 17, 2018, which claims benefit of and priority to U.S. Provisional Application No. 62/454,280, filed Feb. 3, 2017; U.S. Provisional Application No. 62/530,528, filed Jul. 10, 2017; and U.S. Provisional Application No. 62/536,669, filed Jul. 25, 2017 and which are incorporated herein by reference in their respective entireties.

TECHNICAL FIELD

Methods of treating tinnitus.

BACKGROUND

Tinnitus is characterized by an auditory sensation in the absence of external sound. In many cases tinnitus is subjectively perceptual, i.e., only the subject can perceive symptoms. Symptoms of tinnitus include ringing, roaring, static, buzzing, hissing and whistling in one or both ears. The noise may be intermittent or continuous. According to the National Institute on Deafness and other Communication Disorders (NIDCD) approximately 10 percent of the US adult population, or about 25 million Americans, have experienced some degree of tinnitus. According to the American Tinnitus Association, 20 million of these sufferers struggle with burdensome chronic tinnitus, while 2 million have extreme and debilitating cases. Severe tinnitus can lead to depression and other mental health challenges that severely affect the patient and the patient's family members. Therapies such as masking, sound therapy, electrical stimulation, and drugs have shown some benefit. Unfortunately, these treatments may be insufficient and many patients continue to suffer with tinnitus. Therefore, treatment of tinnitus remains a significant need.

Gaboxadol (4,5,6,7-tetrahydroisoxazolo [5,4-c]pyridine-3-ol) (THIP)) is described in EP Patent No. 0000338 and in EP Patent No. 0840601, U.S. Pat. Nos. 4,278,676, 4,362,731, 4,353,910, and WO 2005/094820. Gaboxadol is a selective $GABA_A$ receptor agonist with a preference for δ-subunit containing GABAA receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia. The development was discontinued after the compound failed to show significant effects in sleep onset and sleep maintenance in a three-month efficacy study. Additionally, patients with a history of drug abuse who received gaboxadol experienced a steep increase in psychiatric adverse events.

Although gaboxadol has been suggested for treatment of tinnitus, recent research indicates that gaboxadol GABAA mediated tonic inhibition in auditory thalamus/medial *geniculate* body (MGB) may cause significant tinnitus related increases contralateral to sound exposure. See, e.g., Sametsky et al., Journal of Neuroscience, (Jun. 24, 2015) 35(25):9369-9380.

SUMMARY

Methods of treating tinnitus described herein include administering to a patient in need thereof about 0.05 mg to about 30 mg gaboxadol or a pharmaceutically acceptable salt thereof wherein the method provides improvement in tinnitus. Methods of treating tinnitus described herein include administering to a patient in need thereof about 0.05 mg to about 30 mg gaboxadol or a pharmaceutically acceptable salt thereof wherein the method provides improvement in one or more symptoms of tinnitus. Methods of treating tinnitus described herein include administering to a patient in need thereof about 0.05 mg to about 30 mg gaboxadol or a pharmaceutically acceptable salt thereof wherein the method provides improvement in tinnitus the next day. Methods of treating tinnitus described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating tinnitus are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating tinnitus are described herein which include administering to a patient in need thereof gaboxadol or a pharmaceutically acceptable salt thereof wherein the method provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating tinnitus are described herein which include administering to a patient in need thereof a first pharmaceutical composition comprising gaboxadol or a pharmaceutically acceptable salt thereof and a second pharmaceutical composition comprising gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

DETAILED DESCRIPTION

Figure 1:
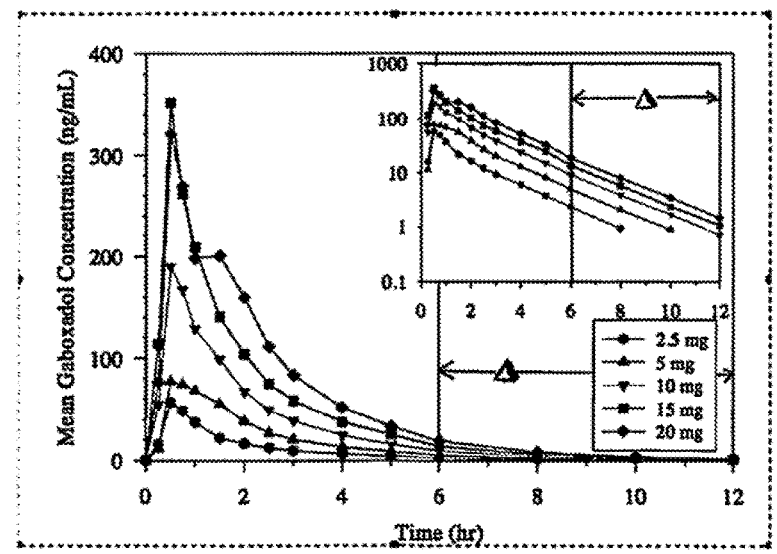
FIG. 1 shows the arithmetic mean plasma concentration-time profiles of gaboxadol following single oral doses (2.5, 5, 10, 15, and 20 mg) as described in Example 1 with horizontal lines Δ indicating the change between 6 and 12 hours.

Described herein are methods of treating tinnitus with gaboxadol or a pharmaceutically acceptable salt thereof. Many pharmaceutical products are administered as a fixed dose, at regular intervals, to achieve therapeutic efficacy. Its duration of action is reflected by its plasma half-life. Gaboxadol is a selective GABAA receptor agonist with a relatively short half-life (t½=1.5 h). Since efficacy is often dependent on sufficient exposure within the central nervous system administration of CNS drugs with a short half-life may require frequent maintenance dosing. Advantageously disclosed herein are methods of treating tinnitus by administration of gaboxadol or a pharmaceutically acceptable salt thereof. For example, in embodiments, methods of treating tinnitus are provided which include administering to a patient in need thereof a pharmaceutical composition including about 0.05 mg to about 30 mg gaboxadol or a pharmaceutically acceptable salt thereof wherein the composition provides improvement for more than 6 hours after administration to the patient.

Methods of treating tinnitus described herein include administering to a patient in need thereof about 0.05 mg to about 30 mg gaboxadol or a pharmaceutically acceptable salt thereof wherein the method provides improvement in one or more symptoms of tinnitus. Methods of treating tinnitus described herein include administering to a patient in need thereof about 0.05 mg to about 30 mg gaboxadol or a pharmaceutically acceptable salt thereof wherein the method provides improvement in tinnitus the next day. Methods of treating tinnitus described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating tinnitus are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating tinnitus are described herein which include administering to a patient in need thereof gaboxadol or a pharmaceutically acceptable salt thereof wherein the method provides an in vivo plasma profile comprising a $AUC_{6-12}$ of less than about 900 ng ng□hr/ml hr/ml and wherein the method provides improvement in the patient for more than 6 hours after administration of the gaboxadol or a pharmaceutically acceptable salt thereof. Methods of treating tinnitus are described herein which include administering to a patient in need thereof a first pharmaceutical composition comprising gaboxadol or a pharmaceutically acceptable salt thereof and a second pharmaceutical composition comprising gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

Embodiments described herein provide that a patient in need thereof is administered a pharmaceutical composition including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylene-salicylic, methanesulfonic, ethane-di sulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about. 0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, methods of treating tinnitus include administering to a patient in need thereof a pharmaceutical composition including about 0.05 mg to about 30 mg gaboxadol or a pharmaceutically acceptable salt thereof.

In embodiments, the pharmaceutical compositions include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

Pharmaceutical compositions herein may be provided with immediate release, delayed release, extended release, or modified release profiles. In embodiments, pharmaceutical compositions with different drug release profiles may be combined to create a two phase or three-phase release profile. For example, pharmaceutical compositions may be provided with an immediate release and an extended release profile.

In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

In embodiments, the pharmaceutical compositions described herein are administered once, twice, or three times daily, or every other day. In embodiments, a pharmaceutical composition described herein is provided to the patient in the evening. In embodiments, a pharmaceutical composition described herein is provided to the patient once in the evening and once in the morning. In embodiments, the total amount of gaboxadol or a pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 5 mg, 10 mg, or 15 mg. In embodiments, the total amount of gaboxadol or a pharmaceutically acceptable salt thereof administered to a subject in a 24-hour period is 20 mg.

In embodiments, provided herein are methods of treating tinnitus including administering to a patient in need thereof a pharmaceutical composition including gaboxadol or a pharmaceutically acceptable salt thereof wherein the composition provides improvement in at least one symptom of the tinnitus. Symptoms may include, but are not limited to, ringing, roaring, static, buzzing, hissing, whooshing, cricket noises, jackhammer noises and/or whistling in one or both ears. The symptoms may be intermittent or continuous. Improvement in tinnitus symptoms through administration of gaboxadol is surprising in view of Sametsky et al., supra.

In embodiments, provided herein are methods of treating tinnitus including administering to a patient in need thereof a pharmaceutical composition including gaboxadol or a pharmaceutically acceptable salt thereof wherein the composition provides improvement of at least one tinnitus symptom for more than 4 hours after administration of the pharmaceutical composition to the patient. In embodiments, the improvement of at least one tinnitus symptom for more than 6 hours after administration of the pharmaceutical composition to the patient is provided in accordance with the present disclosure. In embodiments, improvement of at least one tinnitus symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one tinnitus symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one tinnitus symptom for 12 hours after administration of the pharmaceutical composition to the patient is provided in accordance with the present disclosure.

In embodiments, provided herein methods of treating tinnitus including administering to a patient in need thereof a pharmaceutical composition including gaboxadol or a pharmaceutically acceptable salt thereof wherein the composition provides improvement in tinnitus the next day.

FIG. 1 shows the arithmetic mean plasma concentration-time profiles of gaboxadol following single oral doses (2.5, 5, 10, 15, and 20 mg)(see, Example 1, below) with horizontal lines Δ indicating the change between 6 and 12 hours.

In embodiments, provided herein are methods of treating tinnitus including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 50% and the method provides improvement in the patient for more than 6, 8, 10, 12, 14, 16, 18, 20, 22 or 24 hours after administration. In embodiments, provided herein are methods of treating tinnitus including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 55% and the method provides improvement in the patient for more than 6, 8, 10, 12, 14, 16, 18, 20, 22 or 24 hours after administration. In embodiments, provided herein are methods of treating tinnitus including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 60% and the method provides improvement in the patient for more than 6, 8, 10, 12, 14, 16, 18, 20, 22 or 24 hours after administration. In embodiments, provided herein are methods of treating tinnitus including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating tinnitus including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 70% and the method provides improvement in the patient for more than 6, 8, 10, 12, 14, 16, 18, 20, 22 or 24 hours after administration. In embodiments, provided herein are methods of treating tinnitus including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 75% and the method provides improvement in the patient for more than 6, 8, 10, 12, 14, 16, 18, 20, 22 or 24 hours after administration.

In embodiments, provided herein are methods of treating tinnitus wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating tinnitus wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating tinnitus wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating tinnitus including administering to a patient in need thereof a pharmaceutical composition including gaboxadol or a pharmaceutically acceptable salt thereof wherein the composition provides an in vivo plasma concentration 6 hours after administration which is less than 75% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma concentration 6 hours after administration which is less than 80% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma concentration 6 hours after administration which is less than 85% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma concentration 6 hours after administration which is less than 90% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma concentration 6 hours after administration which is less than 95% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma concentration 6 hours after administration which is less than 100% of the administered dose and provides improvement in the patient for more than 6, 8, 10, 12, 14, 16, 18, 20, 22 or 24 hours after administration.

In embodiments, provided herein are methods of treating tinnitus including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement in one or more symptoms of tinnitus a day after administration. In embodiments, the composition provides an in vivo plasma profile having a $C_{max}$ less than about, e.g., 250 ng/ml, 200 ng/ml 150 ng/ml, or 100 ng/ml and wherein the composition provides improvement in one or more symptoms of tinnitus a day after administration.

In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng·hr/ml. In embodiments, the composition provides improvement in one or more symptoms of tinnitus a day after administration. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement in one or more symptoms of tinnitus a day after administration. In embodiments, the composition provides improvement in one or more tinnitus symptoms for more than 6 hours after administration.

In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement symptoms of tinnitus for more than, e.g., 4 hours, 6 hours, 8 hours, 10 hours, or 12 hours, after administration of the composition to the patient.

In embodiments, provided herein are methods of treating tinnitus including administering to a patient in need thereof an amount of gaboxadol or a pharmaceutically acceptable salt thereof which provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof an amount of gaboxadol or a pharmaceutically acceptable salt thereof which provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof an amount of gaboxadol or a pharmaceutically acceptable salt thereof which provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof an amount of gaboxadol or a pharmaceutically acceptable salt thereof which provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof an amount of gaboxadol or a pharmaceutically acceptable salt thereof which provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof an amount of gaboxadol or a pharmaceutically acceptable salt thereof which provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 75% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 80% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 85% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 90% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 95% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a pharmaceutical composition including gaboxadol or a pharmaceutically acceptable salt thereof wherein the composition provides an in vivo plasma profile having a $AUC_{6-12}$ which is less than 100% of the administered dose and provides improvement in the patient for more than 6, 8, 10, 12, 14, 16, 18, 20, 22 or 24 hours after administration. In embodiments, provided herein are methods of treating tinnitus including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments the first and/or the second pharmaceutical compositions are administered once, twice, or three times daily, or every other day. In embodiments, the first or the second pharmaceutical composition is provided to the patient in the evening. In embodiments, the second pharmaceutical composition includes an amount of gaboxadol that is at least one third of the amount of gaboxadol provided in the first pharmaceutical composition. In embodiments, the second pharmaceutical composition includes an amount of gaboxadol that is at least half of the amount of gaboxadol provided in the first pharmaceutical composition.

In embodiments, the first or the second pharmaceutical composition is provided to the patient once in the evening and once in the morning. In embodiments, the total amount of gaboxadol or pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 10 mg, 15 mg, or 20 mg. In embodiments, the total amount of gaboxadol or a pharmaceutically acceptable salt thereof administered to a subject in a 24-hour period is 20 mg.

In embodiments, the first and/or the second pharmaceutical compositions may be provided with immediate release, delayed release, extended release, or modified release profiles. The first and second pharmaceutical compositions may be provided at the same time or separated by an interval of time, e.g., 6 hours, 12 hours etc. In embodiments, the first and the second pharmaceutical compositions may be provided with different drug release profiles to create a two-phase release profile. For example, the first pharmaceutical composition may be provided with an immediate release profile and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In some embodiments, the first pharmaceutical composition is an immediate release composition. In embodiments, the second pharmaceutical composition is an immediate release composition. In embodiments, the first and second pharmaceutical compositions are provided as separate immediate release compositions, e.g., tablets or capsules. In embodiments the first and second pharmaceutical compositions are provided 12 hours apart.

In embodiments, provided herein are methods of treating tinnitus including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about, e.g., 25%, 30%, 35%, 40%, 45% or 50% less than the first pharmaceutical composition. In embodiments, the composition provides improvement in one or more symptoms of tinnitus a day after administration. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating tinnitus including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptom for more than, e.g., 6 hours, 8 hours or 12 hours after administration of the first pharmaceutical composition.

In embodiments, provided herein are methods of treating tinnitus including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour.

In embodiments, the first pharmaceutical composition provides a dissolution of at least about 80% within the first 20 minutes of administration to a patient in need thereof. In embodiments, the first pharmaceutical composition provides a dissolution of at least about, e.g., 85%, 90% or 95% within the first 20 minutes of administration to a patient in need thereof. In embodiments, the first pharmaceutical composition provides a dissolution of at least 80% within the first 10 minutes of administration to a patient in need thereof.

In embodiments the first and/or the second pharmaceutical compositions are sub therapeutic dosages. A sub therapeutic dosage is an amount of gaboxadol pharmaceutically acceptable salt thereof that is less than the amount required for a therapeutic effect. In embodiments, a sub therapeutic dosage is an amount of gaboxadol pharmaceutically acceptable salt thereof that alone may not provide improvement in at least one symptom of tinnitus but is sufficient to maintain such improvement. In embodiments, the methods provide administering a first pharmaceutical composition that provides improvement in at least one symptom of tinnitus and a second composition that maintains the improvement. In embodiments, after administration of the first pharmaceutical composition the second pharmaceutical composition may provide a synergistic effect to improve at least one symptom of tinnitus. In embodiments the second pharmaceutical composition may provide a synergistic effect to improve at least one symptom of tinnitus.

In embodiments, provided herein are methods of treating tinnitus including administering to a patient in need thereof a pharmaceutical composition including a first pharmaceutical dosage including gaboxadol or a pharmaceutically acceptable salt thereof wherein the composition provides improvement for more than 6 hours after administration and a second pharmaceutical composition including a sub therapeutic dosage of gaboxadol or a pharmaceutically acceptable salt thereof.

Administration of the first and second pharmaceutical compositions may be separated by an interval of time to achieve long-term improvement in at least one symptom of tinnitus. In embodiments, the first and second pharmaceutical composition may be administered 6 hours apart. In embodiments the first and second pharmaceutical composition may be administered 12 hours apart. In embodiments, the first and second pharmaceutical compositions may administered within, e.g., 6 hours, 12 hours, 18 hours, 24 hours etc. In embodiments, the first and second pharmaceutical compositions may administered separated by at least, e.g., 6 hours, 12 hours, 18 hours, 24 hours etc. In embodiments, improvement in at least one symptom of tinnitus for more than 8 hours after administration to the patient is provided. In embodiments, improvement for more than about, e.g., 10 hours, 12 hours, 15 hours, 18 hours, 20 hours, or 24 hours after administration to the patient is provided.

In embodiments, the first pharmaceutical composition and/or the second pharmaceutical composition include about 0.1 mg to about 40 mg gaboxadol or a pharmaceutically acceptable salt thereof. The amount of gaboxadol or a pharmaceutically acceptable salt thereof in the first pharmaceutical composition and the second pharmaceutical composition may be the same or different. In embodiments, the administration of the first and second pharmaceutical composition may provide a synergistic effect to improve at least one symptom of tinnitus.

In embodiments, the first and/or the second pharmaceutical composition include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, or 3 mg to 15 mg gaboxadol or a pharmaceutically acceptable salt thereof.

In embodiments, the first and/or the second pharmaceutical composition include 5 mg to 15 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the first and/or the second pharmaceutical composition include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the first pharmaceutical compositions include 2.5 mg, 5 mg, 7.5 mg, 10 mg, 15 mg, or 20 mg gaboxadol or a pharmaceutically acceptable salt thereof. In embodiments, the second pharmaceutical compositions include 2.5 mg, 5 mg, 7.5 mg, 10 mg, 15 mg, or 20 mg gaboxadol or a pharmaceutically acceptable salt thereof.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of tinnitus measured relative to at least one symptom.

"Improvement in one or more symptoms of tinnitus a day after administration" refers to improvement wherein the beneficial effect of at least one symptom lasts over a period of time, e.g., 6 hours, 12 hours, 24 hours etc.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate aspects of the disclosure herein.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204($s$) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" means a dosage sufficient to alleviate one or more symptoms of a disorder, disease, or condition being treated, or to otherwise provide a desired pharmacological and/or physiologic effect.

"Patient in need thereof" includes individuals that have been diagnosed tinnitus. The methods may be provided to any individual including, e.g., wherein the patient is a neonate, infant, a pediatric patient (6 months to 12 years), an adolescent patient (age 12-18 years) or an adult (over 18 years).

EXAMPLES

The Examples provided herein are included solely for augmenting the disclosure herein and should not be considered to be limiting in any respect.

Example 1

The following Example provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailabilty of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows: Treatment A—one 2.5 mg gaboxadol capsule and 1 matching placebo capsule; Treatment B—one 5 mg gaboxadol capsule and 1 matching placebo capsule; Treatment C—one 10 mg gaboxadol capsule and 1 matching placebo capsule; Treatment D—one 15 mg gaboxadol capsule and 1 matching placebo capsule; and Treatment E—20 mg gaboxadol (two 10 mg gaboxadol capsules). Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, $C_{max}$, $T_{max}$, apparent t½, cumulative urinary excretion, renal clearance, clearance, and steady-state volume of distribution, as appropriate). AUC and $C_{max}$ for gaboxadol were potency adjusted to facilitate comparison of pharmacokinetic data across studies. Table 1 provides the individual potency-adjusted pharmacokinetic parameters of gaboxadol following single oral doses (2.5, 5, 10, 15, and 20 mg).

TABLE 1

Pharmacokinetic parameters for gaboxadol following oral and IV administration

| Parameter | Geometric Mean (N = 10) | | | | | | Slope (90% CI)[††] |
|---|---|---|---|---|---|---|---|
| | 2.5 mg | 5 mg | 10 mg Oral | 10 mg I.V. | 15 mg | 20 mg | |
| $AUC_{0-\infty}$ (ng · hr/mL) | 90 | 171 | 346 | 380 | 539 | 669 | 0.98 (0.95, 1.01) |
| $C_{max}$ (ng/mL)[†] | 61 | 110 | 232 | 212 | 382 | 393 | 0.95 (0.88, 1.02) |
| $T_{max}$ (hr)[‡] | 0.5 | 0.6 | 0.5 | — | 0.5 | 0.6 | |
| Apparent $t_{1/2}$ (hr)[§] | 1.5 | 1.5 | 1.6 | 1.5 | 1.5 | 1.6 | |
| CL/F (mL/min)[¶] | 461 | 488 | 476 | 438 | 469 | 499 | |
| $f_e$(%) | 43 | 45 | 53 | 53 | 50 | 53 | |
| $CL_R$ (mL/min) | 196 | 222 | 250 | 208 | 234 | 265 | |
| F (%) (90% CI)[#] | | | | 92% (0.86, 0.97) | | | |

[†]C(ng/mL) for 10 mg IV.
[‡]Median.
[§]Harmonic Mean.
CL (mL/min) for 10 mg IV.
[#]Bioavailability relative to 10 mg I.V. reference based on pooled dose adjusted (to 10 mg) oral $AUC_{0-\infty}$ values.
[††]Dose proportionality assessment of oral treatments only.

Figure 2:
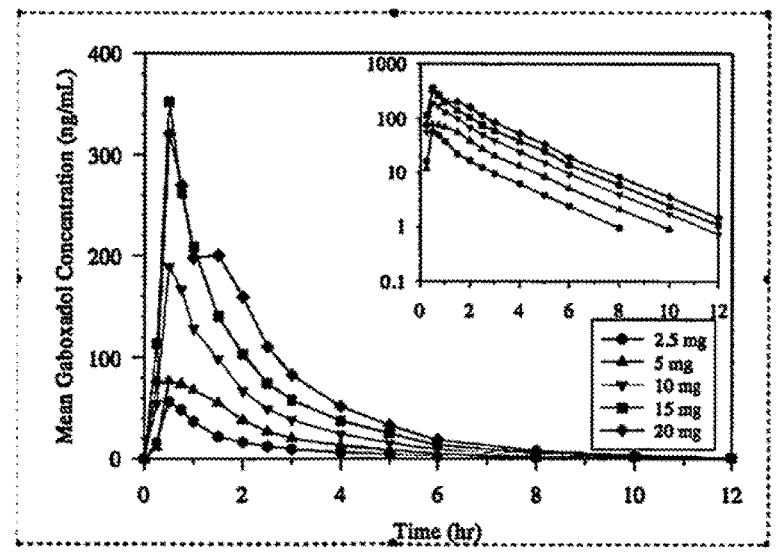
FIG. 2 shows the arithmetic mean plasma concentration-time profiles of gaboxadol following single oral doses (2.5, 5, 10, 15, and 20 mg) as described in Example 1.

FIG. 2 shows the arithmetic mean plasma concentration-time profiles of gaboxadol following single oral doses (2.5, 5, 10, 15, and 20 mg). The bioavailability of gaboxadol is approximately 92%. Plasma $AUC_{0-\infty}$ and $C_{max}$ of gaboxadol show dose proportional increases and appear to be linear over the entire dose range examined, from of 2.5 to 20 mg. The time to peak plasma concentrations ($T_{max}$ 30-60 min) and the half-life (t½ of 1.5 h) for gaboxadol appear to be independent of dose across the gaboxadol dose range of 2.5 to 20 mg. The excretion of gaboxadol is mainly via urine, where 96.5% of the dose is recovered; 75% is recovered within 4 hours after administration.

Example 2

Assessment of Residual Effects Resulting from Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg.

All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit symbol substitution test (DSST), Tracking, Memory tests, Body Sway, and Leeds Sleep Evaluation Questionnaire).

Example 3

Study of Driving Performance after Gaboxadol Administration

This study was a double blind, randomized, placebo and active controlled 5 way cross over study to investigate the effect of evening and middle of the night dosing of gaboxadol on driving performance. The study participants included healthy, male and female subjects between 21 and 45 years of age, with a valid drivers license for at least 3 years.

The effects of gaboxadol on driving performance were investigated using real driving on the road setting. Subjects received 15 mg gaboxadol either in the evening prior to going to bed or at 4 am in the middle of the night following a wake-up call. Following a cognitive and psychomotor test battery, the driving test started at 9 am and lasted for one hour. Gaboxadol 15 mg had a clinically relevant impairing effect on driving following middle-of-the-night administration.

Following the evening dose, a statistically significant effect of gaboxadol 15 mg was observed on driving. However, this effect was less than the effect observed at a 0.05% blood alcohol concentration, the concentration limit at which driving is prohibited in most European countries. There was generally a numerically greater effect following zopiclone (7.5 mg) and zolpidem (10 mg) administered in the evening and in the middle of the night, respectively. Both the evening and the middle-of-the-night dose of gaboxadol were well tolerated with the most frequent adverse events being dizziness, nausea and somnolence for the middle-of-the-night treatment and headache and somnolence for the evening treatment.

Subjects on the active reference zopiclone had a numerically greater effect in the same test. There was no effect on memory test, body sway, DSST or critical tracking, whereas zopiclone had effect on several of these tests.

Example 4

Study of Daytime Performance after Sleep Restriction

This study was a 4-night, parallel-group, randomized, double-blind (with in-house blinding), placebo-controlled, fixed-dose study to assess the effects of gaboxadol on daytime performance in healthy adults subjected to a 5-hour sleep restriction. The study included a 2-night single-blind placebo run-in period, a 4-night double-blind treatment period during which sleep was restricted to 5 hours and a 2-night single-blind placebo run-out period. The study included healthy male and female volunteers 18 to <55 years of age.

2-night run-in period: All patients received placebo
4-night double-blind treatment period: Patients were randomized to gaboxadol 15 mg or matching placebo
2-night run-out period: All patients received placebo The primary endpoints included observations based on the Multiple Sleep Latency Test (MSLT) and Slow Wave Sleep (SWS) assessment. The primary objective was to evaluate the efficacy of gaboxadol (15 mg) compared to placebo in reducing daytime sleep propensity as measured by MSLT. The gaboxadol subjects had significantly less daytime sleepiness during the Sleep Restriction period than did placebo subjects (p=0.047, 1 sided). The MSLT was on average 2.01 minutes longer for subjects treated with gaboxadol (15 mg) than for those with placebo on the last two Sleep Restriction days.

In addition, a secondary objective was to evaluate the efficacy of gaboxadol compared to placebo in increasing the amount of slow wave sleep (SWS) during the last 2 nights of sleep restriction. Subjects receiving gaboxadol experienced significantly more SWS during the Sleep Restriction period than did placebo subjects (p<0.001, 1 sided).

Moreover, subjects treated with gaboxadol on average had 20.53 minutes of SWS longer than those treated with placebo on the last two Sleep Restriction nights.

Finally, this study examined the efficacy of gaboxadol compared to placebo during the last 2 nights/days of sleep restriction in: (1) improving memory and attention as assessed by a neurobehavioral battery; (2) reducing subjective sleepiness as measured by the Karolinska Sleepiness Score (KSS); (3) altering sleep parameters (e.g., total sleep time, latency to onset of Slow Wave Sleep (SWS), slow wave activity (SWA); and (4) reducing biological stress typified by increased heart rate variability, and decreased cortisol levels and decreased catecholamine levels, as well as decreased body temperature.

There was a trend towards less subjective daytime sleepiness for the gaboxadol subjects during the Sleep Restriction period as compared with placebo subjects. The Karolinska Sleepiness Score (KSS) was on average 0.68 less for subjects treated with gaboxadol than for those treated with placebo on the last two Sleep Restriction days (p=0.058, 1 sided) as evaluated by a Longitudinal data analysis (LDA) model with adjustment for baseline KSS, gender, and age. A supportive analysis using covariance (ANCOVA) also supports this finding. The effect sizes computed for the neurocognitive battery showed that there was no strong evidence that gaboxadol improves daytime performance. There were no differences between gaboxadol and placebo with respect to biophysiological measures of stress (heart rate variability, cortisol levels, catecholamine levels, body temperature).

Compared with placebo, gaboxadol has a protective effect on reducing daytime sleepiness as measured by the MSLT on the last 2 days of 4-nights of sleep restriction. Compared with placebo, gaboxadol increases the amount of slow wave sleep (SWS) during the last 2 nights of 4-nights of sleep restriction.

Example 5

Prospective Assessment of the Efficacy of Gaboxadol in Patients with Tinnitus

This study is designed to determine whether gaboxadol leads to an improvement in tinnitus. The primary objective of this study may be to evaluate the safety and tolerability from Baseline to Week 6 and Week 12 of gaboxadol in adult subjects with tinnitus across different dose levels and in two dosing schedules. The following dosing schedules may be tested against placebo: (1) Once daily (o.d.): An evening dose, titrated to the target dose of 15 mg unless not tolerated; and (2) Twice daily (b.i.d.): Evening and morning doses titrated to the target doses of 15 mg evening dose and 10 mg morning dose unless not tolerated.

The Safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine); (4) Suicidality assessed by ABC-Irritability Subscale; (5) EEG (change in background frequency, intensity of epileptiform discharges); and/or (6) Caregivers may maintain an electronic seizure diary (on same device as sleep log).

The secondary objective of this study may include the identification of a set of parameters that may best characterize the efficacy of gaboxadol in adult tinnitus subjects for subsequent efficacy trials. These tests may be administered at four full day site visits (Screening, Baseline, Interim and End of Treatment) by an appropriately trained professional to provide the test to an adult tinnitus patient. Assessments may be based on patient's perception of symptoms. Tinnitus loudness-visual analogue scale (VAS) [Time Frame: each week: the time between the questionnaire results at the beginning and compared to the results after each week following initial administration. Tinnitus loudness scale: A range of 1-10 scale, the patients choose which number reflects the loudness of the subjective tinnitus which the patients suffer from, the higher the number—the louder the tinnitus. Tinnitus suffer scale: A range of 1-10 scale, the patient choose which number reflects the best the degree in which the tinnitus causes the patient to suffer, the higher the score—the worse is the tinnitus.

Evaluation of sleep may include analysis by actigraphy to measure: (1) Sleep Onset Latency (SOL); (2) Total Sleep Time (TST); (3) Wake After Sleep Onset (WASO)=total # of wake epochs after sleep onset; (4) Nocturnal Awakenings (NA); and/or (5) Sleep Efficiency=total sleep time (TST) of time in bed (TIB). Additional evaluation of sleep may include analysis of parent/caregiver logs of sleep patterns that may include: (1) bed time; (2) time of sleep onset; (3) number and duration of awakenings; (4) number of disruptive behavior; (5) time of last awakening; and (6) daytime sleepiness.

This study may include three treatment groups. For example, a total of approximately 75 subjects may be enrolled and at the completion of the study, there may be approximately 25 subjects in each of the three treatment groups: 1) single evening dose 2) morning and evening dose and 3) placebo.

Figure 3:
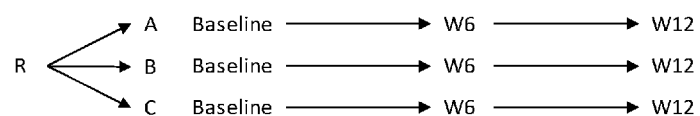
FIG. 3 schematically illustrates treatment of three groups over a proposed 12 week course of treatment: 1) single evening dose 2) morning and evening dose and 3) placebo.

All subjects may receive a morning dose (either active or placebo) and an evening dose (either active or placebo) during the entire duration of treatment. For example, as illustrated in FIG. 3, two dosing schedules of gaboxadol may be tested: a single evening dose (o.d.; Schedule A) and a morning plus evening dose (b.i.d; Schedule B) designed to provide a more sustained exposure. Schedule C is morning and evening placebo. All subjects may be up-titrated to the target dose unless this target dose is not tolerated (titration conventions described below). All subjects may receive treatment for a maximum of 12 weeks at their optimal tolerated dose.

Doses may be progressively increased in 5 mg increments (active or placebo) to a target dose of 3 capsules evening dose in schedule A and B, and 2 capsules morning dose in schedule B. Each dose escalation may be performed after adequate tolerability has been assessed by caregiver and investigator. For example, treatment initiation at Day 1 with 1 capsule (active (Act) or placebo (Plc)) in the evening. Then target up-titration may begin at Day 3 (window +2 days): If no adverse event (AE) related to the study drug is observed by caregiver and/or the investigator, another capsule (active or placebo) is added in the evening. Again at Day 7 (window +2 days), Day 10 (window +2 days and Day 14 (window +2 days) if no AE related to the study drug is observed by caregiver and/or the investigator, another capsule (active or placebo) may be added in the morning. Table II below provides a graphic illustration of the titration schedule.

TABLE II

Titration Schedule

| Schedule/Time | | Days 1 to 2 | Days 3 to 6 | Days 7 to 9 | Days 10 to 13 | Day 14* |
|---|---|---|---|---|---|---|
| Schedule A | Evening | 5 mg<br>1 Capsule | 10 mg<br>2 Capsules | 15 mg<br>3 Capsules | 15 mg<br>3 Capsules | 15 mg<br>3 Capsules |
| | Morning | None | None | None | Placebo<br>1 Capsule | Placebo<br>2 Capsules |
| Schedule B | Evening | 5 mg<br>1 Capsule | 10 mg<br>2 Capsules | 15 mg<br>3 Capsules | 15 mg<br>3 Capsules | 15 mg<br>3 Capsules |
| | Morning | None | None | None | 5 mg<br>1 Capsule | 10 mg<br>2 Capsules |
| Schedule C | Evening | Placebo<br>1 Capsule | Placebo<br>2 Capsules | Placebo<br>3 Capsules | Placebo<br>3 Capsules | Placebo<br>3 Capsules |
| | Morning | None | None | None | Placebo<br>1 Capsule | Placebo<br>2 Capsules |

*To end of study treatment period

Slowed up-titration or delayed up-titration will be acceptable if tolerability does not allow immediate further dose-escalation at any of the above detailed days (3, 7, 10, 14). Down-titration in the case tolerability is not acceptable (e.g., somnolence, dizziness, change in behavior) after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (2 capsules in the morning and 3 in the evening) the subject may be kept stable until End of Treatment visit (week 12) unless intolerability requires down-titration.

All subjects will be screened for participation in the study up to 28 days prior to the first dose administration. Inclusion criteria may include one or more of the following: (1) Age ≥18 years, ≤40 years; (2) Must possess a clinical diagnosis of tinnitus. Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Those skilled in the art will recognize, or be able to ascertain using no more than routine experimentation, many equivalents to the specific embodiments described herein. Such equivalents are intended to be encompassed by the claims.

What is claimed is:

1. A method of treating tinnitus comprising administering to a patient in need thereof about 0.05 mg to about 30 mg gaboxadol or a pharmaceutically acceptable salt thereof, wherein the method provides improvement in one or more symptoms of tinnitus in the patient and the improvement is provided for more than 6 hours after administration.

2. The method of claim 1, wherein the patient is administered a composition comprising about 1 mg to about 15 mg gaboxadol or a pharmaceutically acceptable salt thereof.

3. The method of claim 1, wherein the patient is administered a composition comprising about 1 mg to about 10 mg gaboxadol or a pharmaceutically acceptable salt thereof.

4. The method of claim 1, wherein the patient is administered a composition comprising about 1 mg to about 5 mg gaboxadol or a pharmaceutically acceptable salt thereof.

5. The method of claim 1, wherein the in vivo plasma profile of the patient 6 hours after administration of the gaboxadol or pharmaceutically acceptable salt thereof is reduced by more than 50%.

6. The method of claim 1, wherein the $AUC_{6-12}$ of the patient 6 hours after administration of the gaboxadol or pharmaceutically acceptable salt thereof is less than 75% of the administered dose.

7. The method of claim 1, wherein the method provides improvement in at least one symptom selected from the group consisting of ringing, roaring, static, buzzing, hissing, whooshing, cricket noises, jackhammer noises and whistling, in one or both ears.

8. The method of claim 1, wherein the method provides improvement in the patient for more than 8 hours.

9. The method of claim 1, wherein the composition provides improvement in the patient for at least 12 hours.

10. The method of claim 1, further comprising administering from about 1 mg to about 30 mg clobazam or a pharmaceutically acceptable salt thereof to the patient.

11. The method of claim 10, wherein the amount of clobazam or a pharmaceutically acceptable salt thereof is 5 mg to 20 mg.

12. The method of claim 10, wherein the amount of clobazam or a pharmaceutically acceptable salt thereof is 10 mg.

13. A method of treating tinnitus comprising administering to a patient in need thereof gaboxadol or a pharmaceutically acceptable salt thereof wherein the method provides an in vivo plasma profile comprising a $C_{max}$ less than about 400 ng/ml and wherein the method provides improvement in the patient for more than 6 hours after administration of the gaboxadol or a pharmaceutically acceptable salt thereof.

14. A method of treating tinnitus comprising administering to a patient in need thereof gaboxadol or a pharmaceutically acceptable salt thereof wherein the method provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof.

15. The method of claim 1 wherein the method provides improvement in the patient for more than a day after administration.

* * * * *